Figure 1:
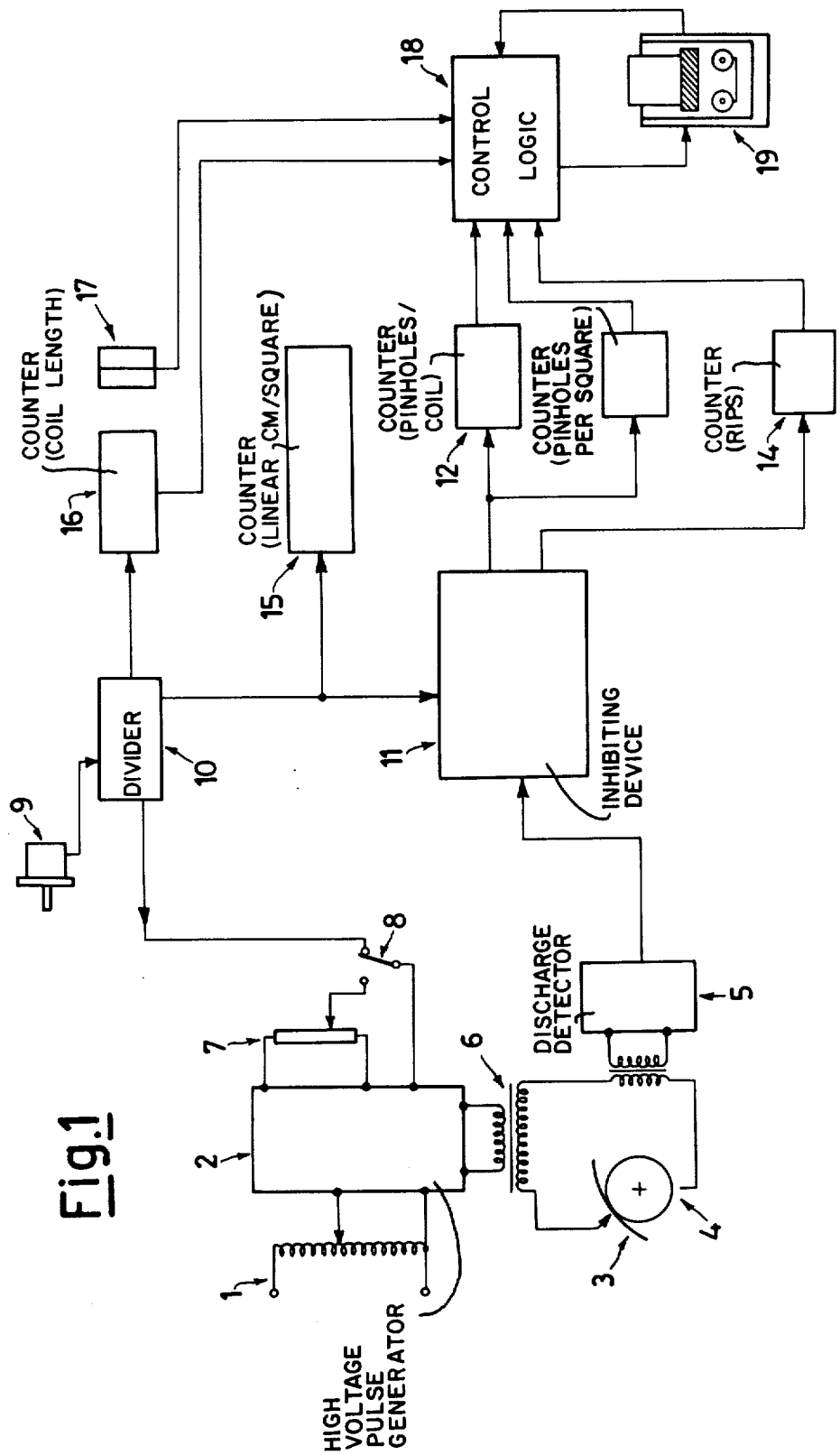

United States Patent [19]

Viganò et al.

[11] 4,229,645
[45] Oct. 21, 1980

[54] DETECTOR AND RECORDER OF HOLES AND DISRUPTIONS IN PLASTIC MATERIAL SHEETS AND WEBS

[75] Inventors: Carlo Viganò, Cavaria; Francesco Quattrone, Milan; Erio Toffanetti, San Donato Milanese, all of Italy

[73] Assignees: Anic S.p.A., Palermo; Costruxioni Elettriche Automatiche Impianti (C.E.A.I), Busto Arsizio, both of Italy

[21] Appl. No.: 906,219

[22] Filed: May 15, 1978

[30] Foreign Application Priority Data

May 20, 1977 [IT] Italy .............................. 23804 A/77

[51] Int. Cl.³ .......................................... G06M 7/00
[52] U.S. Cl. ................................ 235/92 QC; 73/159; 235/92 SB; 235/92 PK; 235/92 DN

[58] Field of Search ........ 235/92 QC, 92 DN, 92 FP, 235/92 PK, 92 SB, 92 EL; 340/259; 73/159, 157

[56] References Cited

U.S. PATENT DOCUMENTS

| 3,571,574 | 3/1971 | Gerber ............................ 235/92 PK |
| 3,729,619 | 4/1973 | Laycak et al. ................. 235/92 DN |
| 3,778,802 | 12/1973 | Wallace ..................... 73/157 |
| 3,983,371 | 9/1976 | Siranni et al. ................. 235/92 QC |

*Primary Examiner*—Joseph M. Thesz
*Attorney, Agent, or Firm*—Morgan, Finnegan, Pine, Foley & Lee

[57] ABSTRACT

A device is disclosed for continuously counting up the pinholes and the rips (continuous disruptions) in a film or web of plastic materials, said device having a gating circuit which is capable of distinguishing the pinholes from the rips thus giving a more reliable indication than was possible with the conventional devices also based on detection of electric discharges.

4 Claims, 2 Drawing Figures

DETECTOR AND RECORDER OF HOLES AND DISRUPTIONS IN PLASTIC MATERIAL SHEETS AND WEBS

This invention relates to a device which identifies, detects, totals and records pinholes and possible cuts and disruptions on plastic material sheets.

Such an identification, together with the subsequent operations, is carried out during the winding of the films on the takeup drums.

During manufacture of sheets and webs of plastic material pinholes, cuts or disruptions may occur on such articles and, if such defects are numerous or are clustered with a certain density, they make the articles defective and unsuitable for their intended use.

Thus, it has become necessary to be able to detect the exact positions and the possible accumulation of the defects which occur so as to discard the defective sections.

Pinhole-detecting devices have already been suggested and these exploit the dielectric properties of the plastic material films.

More exactly, such devices signal the occurrence of the pinholes by an electric discharge which is experienced in correspondence with the pinholes whenever the film is caused to run between a high-voltage electrode (from 2 to 25 kV) and a conductive roller which is grounded (the unaffected film, being a dielectric, does not otherwise allow the flow of electricity between the electrode and the conductor).

However, the occurrence of electrostatic charges on the films, which is usually experienced during the film manufacture on account of frictional sliding, causes a number of disturbances in the detection of the pinholes because electric sparks are signalled continuously.

In addition, the occurrence even of a single pinhole originates more than one discharge inasmuch as the first discharge is experienced when the pinhole reaches the minimum distance from the electrode which is required to prime the spark and the discharges continue until the pinhole, passing beneath the electrode goes beyond such minimum distance.

In addition, the existence of disruptions gives rise to an incorrect detection of the defects of a film since such disruptions are signalled as if they were pinhole sequences.

It has now been found that it is possible to suppress the signalling of electrostatic discharges and to identify the cuts as such.

As a matter of fact, the electrostatic discharges have a low intensity of current, whereas those between the electrode and the conductor roller have a higher intensity.

A low-impendance transformer, with a gating circuit divides the two kinds of discharges and delivers to the detecting circuit only those signals which have a high current intensity.

In order that cuts may be identified, provision has been made of an appropriate inhibiting device the operation of which is described by way of summary hereinafter. p The device is so preset as to be able to count, by counting the relative discharges, the pinholes contained in a film coil and to identify their positions. It permits discrete discharges to be signalled and counted, whereas it switches the sequence of discharges to another counter. As a matter of fact, when a discharge occurs, which is signalled and recorded by the specially provided counter, the circuit reacts in such a way that no further consecutive discharges can be passed onto the counter until a certain portion of pinhole-free film has run past, and simultaneously switches the consecutive discharges to the rip-counting device.

As soon as the rip-counter receives a number of consecutive discharges equal to or higher than a preselected value which has been preset on the same counter in advance, the counter will receive a pulse which will be the signal corresponding to a torn place, the latter being then recorded on the same counter.

If the number of consecutive discharges is below the preset value, these discharges are counted as a single pinhole.

Subsequently to the counting of a torn place and after the counter has received a preselected number of voltage pulses without any discharge having been detected, that is, after that a section of unaffected film has run past, the circuit will be reset which will permit discharges due to isolated pinholes to be detected and counted. Thus, in correspondence with each pinhole there is the recordal and the counting of the relative discharge on the specially provided counter, whereas the rip counter will count and record the discharges in sequence which correspond to a torn place.

At any rate, each discharge is counted and recorded with reference to its position on the film, to the total number of pinholes which has already been counted and to the code number of the film coil which is being processed.

The apparatus in question is essentially composed by two units, viz.:
a high-voltage pulse generator, and
a checkup and recordal unit.

The first unit generates voltage pulses at the fixed frequency of 50 hertz for calibrating the instrument and voltage pulses at a frequency which varies from 0 to 1,500 hertz consistently with the feed speed of the film, as used for work.

The second unit effects a plurality of operations, viz.:

(1) It counts and displays the millimeters, or meters of web which have been checked. Generally speaking, these data are based on a conventional surface unit for films or webs, and exactly the square, which is tantamount as 9.24 square meters. The length of the web being checked is generally the length, in meters or millimeters, which corresponds to one square (as a matter of fact each film or web can have a different width and thus different lengths in decimal units, such as meters or millimeters correspond to one square).

(2) It counts and displays the number of pinholes per square.

(3) It counts and displays the total number of pinholes for a coil.

(4) It prevents the multiple and nonsignificant countup in correspondence with broad holes or torn places in the web and counts the torn places.

(5) It measures and displays the coil length.

(6) It prints on a specially provided tabulate the previously counted and displayed counts, viz.:
number of pinholes per square
number of rips per square
number of pinholes per coil
web length on coil and code number of the coil.

(7) It preselects the sensitivity of the checkup operations, that is, the number of electric pulses emitted per millimeter of web or of film.

Figure 2:
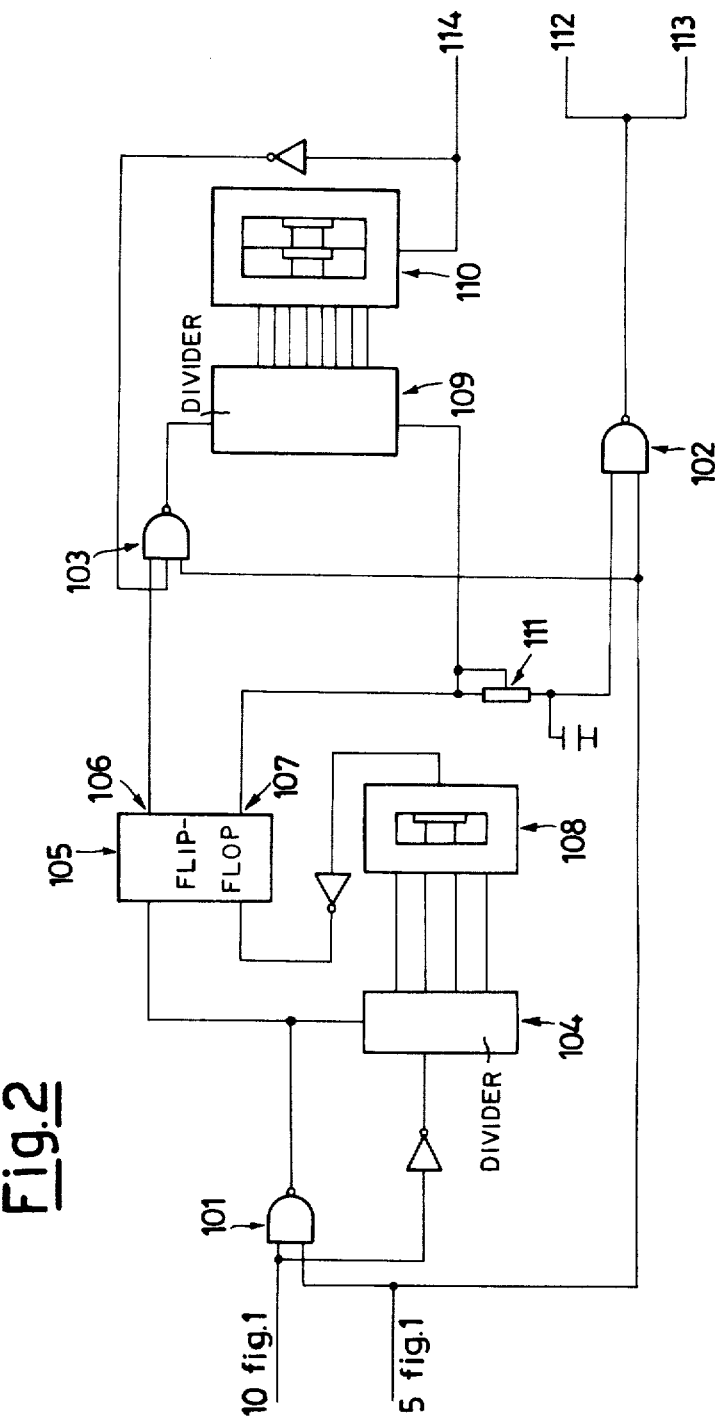

FIG. 1 of the accompanying drawings shows a block diagram of the entire implementation and FIG. 2 shows the block diagram of the inhibiting unit.

In FIG. 1, the numeral 1 is for the source of electric power, 2 is the high voltage pulse generator, 3 is the high-voltage electrode, 4 the roller on which the film or web runs towards the takeup, 5 is a discharge detector which is composed of a transformer for detecting the discharges between the electrode and the roller, such detector being equipped with a logic circuit for the formation of the pulses to be delivered to the control and recordal unit. Detector 5 is connected to the generator 2 and the electrode 3 through the step-up transformer 6.

The frequency of the pulses is adjusted through the governor 7 which can be controlled either manually or automatically (by means of a switch 8) as a function of the required sensitivity. The sensitivity, that is the control interval given by the apparatus, is determined by a divider 10 which can be set with a counting device, a two-digit counter from 1 to 99 which divides by the preset number the number of pulses per second coming from the rotopulser 9 keyed to the roller 4, the number of pulses per millimeter of film running on the roller being thus established. The numeral 11 is the inhibiting device which is diagrammatically shown in FIG. 2.

The other blocks of the layout are the counters which display the data relating to each measurement and are connected to the remainder of the implementation, from which they receive the signals through the sensitivity adjustment device and the inhibiting device.

These apparatus indicate, respectively, the following data: 12 is for the number of pinholes per coil, 13 is for the number of pinholes per square, 14 is for the number of rips per square, 15 is for the number of linear centimeters of film per square, 16 is for the number of meters of film in the coil, 17 is for the individual code number of the coil, and 18 is the control logic which transfers the data obtained on the printout device 19 which gives the tabulates.

FIG. 2 shows the inhibiting circuit, in which 101, 102 and 103 are the gates, that is the outputs of the pulses towards the various circuits. The reference 104 is the divider (it divides by ten) on which the number of voltage pulses as received without detection of discharge is reduced. 105 shows the latching and enabling flip-flop of the outputs towards the several counter circuits, with automatic alternate setting of the outputs 106 and 107 at the levels 1 and 0. 108 is the coincidence device for transferring the commands between 104 and 105. 109 is the divider (by 100) on which is set the maximum number of consecutive discharges which correspond to a rip. The numeral 110 indicates the preselector of the number of consecutive discharges which is considered as corresponding to a rip. 111 is a condenser rheostat.

In the normal operation, that is when an unimpaired film or web passes, the discharge command is present at the inputs of 101 and of 104. The flip-flop 105 is reset continuously by the output of the divider 108 and presents the outputs 106 at the level zero and the 107 output at the level 1.

The output 106 at level zero latches and keeps latched the gate 103, thus latching the rip counter circuit.

The output 107 at the level 1 enables the gate 102 and thus also the pinhole counting circuit. As a pinhole passes, in addition to the discharge command coming from the divider 10 of FIG. 1, there is the passage of the signal of detected discharge. The signal "detected discharge" passes through the gate 102 and is counted by the pinhole counter (pinholes per square or per meter and total pinholes) and simultaneously the signal passes through the gate 101 and is returned to the flip-flop thus setting it with the output 106 at the level 1 and the output 107 at the level zero.

The output 107 set in this way latches after a delay time caused by the rheostat condenser 111, the gate 102 thus preventing a possible subsequent discharge from being counted. If sequential discharges are experienced, a signal is generated, which maintains the flip-flop in the latched position and simultaneously prevents the divider 104 from counting so that a continuous series of discharges is counted as a single discharge.

Under these conditions, the output 106 of the flip-flop enables the gate 103 and the counter of the divider 109 counts all the inhibited discharges. As soon as the number preset on the preselector 110 is reached, a pulse emerges which is counted as a rip and thus is displayed on the counter 14 of FIG. 1, and simultaneously locks the gate 103 to prevent the count of a number of rips in the case of a continuous discharge. The initial circuit is reset when the divider 104 has received a number of discharge commands (voltage pulses with no detected discharges) equal to the number set on such divider. As soon as such a number is attained, the flip-flop is reset with the output 106 at the level zero and the output 107 at the level 1. Thus the gate 102 is enabled again and the circuit is in readiness for counting another possible pinhole.

We claim:

1. A device for detecting pin holes on moving films or webs of plastic materials comprising:

a high voltage electrode and a grounded roller between which the web passes during coiling;

means coupled to the roller for detecting pin holes in the web based on electrical discharges; and means for counting rips in the web, said rip counting means including an inhibiting device coupled to said detecting means and comprising a flip-flop, a first counter for recording pin holes by counting discrete electrical discharges, a second counter for recording consecutive electrical discharges indicative of a rip, gating means responsive to said flip-flop for coupling signals of said detecting means to said first and said second counters, said gating means including means responsive to a rate of occurrence of consecutive discharges to set said flip-flop for switching signals of said detecting means to the second counter, and means for resetting the flip-flop to signal discrete discharges after a preselected length of film having no defects has run past.

2. A device in accordance with claim 1 further including:

means for supplying voltage pulses to the electrode at a frequency which varies in accordance with the feed speed of the web, and, means for counting the length of the web passing the electrode.

3. A device in accordance with claim 2 further including:

a control logic circuit coupled to the counting means and a print-out apparatus controlled by said logic circuit to provide a printed count of pinholes and rips.

4. A device in accordance with claim 2 wherein:

the means for detecting pin holes comprises a transformer, and the device further includes a governor for controlling the frequency of high voltage pulses to the electrode to provide the desired sensitivity.

* * * * *